United States Patent [19]

Okada et al.

[11] Patent Number: 4,704,108

[45] Date of Patent: Nov. 3, 1987

[54] WATER CONTENT SENSING AND INFORMING SYSTEM FOR A DISPOSABLE DIAPER

[75] Inventors: Shigeru Okada; Katsutoshi Rokuta, both of Kochi, Japan

[73] Assignee: Nippon Kodoshi Corporation, Kochi, Japan

[21] Appl. No.: 831,288

[22] Filed: Feb. 20, 1986

[30] Foreign Application Priority Data

Sep. 26, 1985 [JP] Japan .................... 60-147851[U]

[51] Int. Cl.[4] ............................................ A61B 19/00
[52] U.S. Cl. .................................. 604/361; 604/358; 128/638
[58] Field of Search ........................................ 604/361

[56] References Cited

U.S. PATENT DOCUMENTS

| | | | |
|---|---|---|---|
| 3,460,123 | 8/1969 | Bass | 604/361 |
| 4,205,672 | 6/1980 | Dvorak | 604/361 |
| 4,356,818 | 11/1982 | Macias et al. | 604/361 |
| 4,583,546 | 4/1986 | Garde | 604/361 |

Primary Examiner—C. Fred Rosenbaum
Assistant Examiner—Sherri E. Vinyard
Attorney, Agent, or Firm—Shlesinger Arkwright & Garvey

[57] ABSTRACT

Water content sensing and informing system for the disposable diaper composed of a water permeable inner sheet, a water absorber and a water impermeable outer sheet, comprises a water content sensing means consisting of a water impermeable sheet, and a first and second metal layers, the first metal layer being formed on one side surface of the water impermeable sheet, and the second metal layer being formed on the other side surface of the sheet and an informing means, electrically connected to the above two metal layers, for informing that the water content in the diaper exceeds a specific level in response to the change of the electric conductivity between the first metal layer and the second metal layer. The water content sensing means is disposed in any suitable section in the diaper such as in the water absorber, between the water absorber and the water impermeable outer sheet, or between the water absorber and the water permeable inner sheet and is adapted to be assembled with the diaper by means of a pressure welding or an adhesive at the same manufacturing process.

13 Claims, 10 Drawing Figures

WATER CONTENT SENSING AND INFORMING SYSTEM FOR A DISPOSABLE DIAPER

BACKGROUND OF THE INVENTION

1. Field of the Invention

The present invention generally relates to a water content sensing and informing system for a disposable diaper. In its particular aspects, the present invention, relates to a water content sensing and informing system for a disposable diaper, that provides convenience and comfort to the person who wears it such as babies or bed ridden aged people, and instantly informs an individual when the diaper is substantially saturated and thus ready for changing.

2. Description of the Prior Art

Recently, the number of aged people has been increased owing to the progress of medical science, and also the number of bed ridden people has tended to increase simultaneously. In nursing homes for the elderly, it is estimated that at least 30 percent of the patients are bed riddens. In caring for such patients, the treatment of excrements has caused serious problems. It is obvious that providing a system for treating the excreation of urine would lessen the distress and burden for the patients and nursing home employees.

Conventionally, two systems have been commonly used for such urine treatment. The first is a diaper treatment using a diaper or napkins to absorb the excreted urine. The other is a continuous urine excretion treatment using an urethral catheter such as balloon catheter. The latter urine treatment system is continuously attached to the urinating organ of the patient.

The above mentioned diaper treatment will be discussed in detail as the present invention is related to this treatment. In hospitals or nursing homes, the time for changing diapers of the patients is fixed at certain intervals since the nurse has no way to know the urinating pattern of all of the patients. However, the systematic changing of patient's diapers at periodic intervals results in patients being left with a wet diaper for a long time causing discomfort and pain owing to a diaper rash, cooling, bed sores and the like.

In order to determine the individual urination pattern of patients, various methods to detect the water content in the diaper have been provided.

In our previous invention, Japanese Patent Application For Utility Model No. 57-165692, the present inventors have proposed a specific diaper comprising a water permeable inner sheet, a water impermeable outer sheet, a water absorber disposed between the inner and outer sheets and a water sensing means composed of a plurality of electroconductive metal layers or a stripe of electroconductive paper which is laminated on a paper or a plastic film.

Further, our previous invention Japanese Patent Application for Utility Model No. 58-202267, as shown in FIG. 7 and FIG. 8, discloses a modified example of the above diaper. The modified diaper comprises a plurality of metal layers (for convenience sake, two layers 2,2 are shown in these drawings) adhered to the surface of the water impermeable outer sheet 1 in order to detect the water content in the water absorber, not shown, by means of the change in electric conductivity between the two metal layers 2,2.

In addition to these inventions, the present inventors have provided a capacitor type water content detecting means as shown in FIG. 9 and FIG. 10 (Japanese Patent Application No. 59-128238 and No. 59-143649). Illustrated, in the figures, is a pair of metal thin layers 4 and 5 adhered to the surface of the water impermeable outer sheet 1. Layer 5 is covered with an insulating layer 6 so as to form the structure of a capacitor in this diaper. The electrostatic capacity of this capacitor corresponds to the amount of the water absorbed in the water absorber, not shown, of the diaper. The degree of wetness can be determined by detecting the change in the electrostatic capacity with well-known measuring devices. Accordingly, an information signal is generated only when the degree of wetness of the diaper reaches a predetermined level corresponding to the condition when the diaper should be changed. An AC voltage is applied to the capacitor, and the capacitor is connected to a compact oscillator, through lead wires, to transmit the information signal to a receiver located remote from the oscillator. This arrangement results in a significant increase in the consumption of electric power. Further, the capacitor type water content detecting system is extremely expensive to manufacture.

On the other hand, with the former device, which can detect the water content by monitoring the change in electric conductivity of electrodes, a diaper in the soiled state is readily detected by means of an electrical device. Therefore, the patients are spared any discomfort or pain. Although, this device can not determine the degree of wetness of the diaper, and the water detecting signal may be often generated even if the diaper is only slightly soiled. A small amount of water may be spread over a plurality of metal layers adhered on the same surface, so that the electric conductivity between the metal layers may change, and thus the water detecting signal may be transmitted. Further, an inadvertent signal may be generated owing to breakage or short-circuit between the metal layers as the patient or baby moves. These facts cause another problem in that the diapers are prematurely disposed. Nevertheless, this device does not require the lamination of the electric insulating layer on the metal layer, and thus its manufacturing process is not as complicated, and the consumption of electric power is lower than the above capacitor type water content detecting device.

OBJECT OF THE INVENTION

It is an object of the present invention to provide a water content sensing and informing system for a disposable diaper which can sense and inform the wetness of the diaper at the moment when the diaper needs to be changed.

Another object of the present invention is to provide a water content sensing and informing system for a disposable diaper which can be manufactured in a simple manner and at a relatively low cost.

Yet another object of the present invention is to provide a water content sensing and informing system for a disposable diaper which is free from premature detection owing to the breakage of water sensing section as the patient moves.

Another object of the present invention is to provide a water content sensing and informing system for a disposable diaper with lower energy consumption.

A further object of the present invention is to provide a water content sensing and informing system for a disposable diaper which can transmit the detected information to a remote place.

SUMMARY OF THE INVENTION

To accomplish the above mentioned objects, a water content sensing and informing system for a diaper according to the present invention comprises the following structure.

The disposable diaper primally consists of a water permeable inner sheet, a water impermeable outer sheet and a water absorber interposed between the inner and outer sheets. The disposable diaper further comprises a water content sensing means which is installed in a proper position defined such as between the water absorber and the water impermeable outer sheet. The water content sensing means is composed of a water impermeable sheet, a first metal layer formed on one side surface of the water impermeable sheet and a second metal layer formed on the other side surface. The first and second metal layers are connected to an informing system through lead wires.

The informing system comprises an oscillator, which is activated in response to the change of electric conductivity between the first and second metal layers, when the wetness of the diaper exceeds a predetermined level. A signal is transmitted to a receiver located at a remote place which provides the information to the nursing personnel by acoustic or visual information or the like.

The oscillator for this informing means may be provided in an extremely compact size and packed in a water proof container and connected to the diaper with clip terminals.

According to the above mentioned structure and composition, the present invention provides various advantages as follows.

When the amount of water is so small that it is completely absorbed in the water absorber of the diaper, the water does not flow to the bottom surface of the water impermeable sheet. The first and second metal layers are respectively formed on the top and bottom surfaces of the water impermeable sheet so as to isolate the first and second metal layers electrically, so that the electric conductivity between the first and second metal layers is not changed. If the water increases and exceeds over a specific level such that the water is not completely absorbed in the water absorber, the water will flow over the edges of the water impermeable sheet and spread to the bottom surface of the water impermeable sheet. Thus, the electric conductivity between the first and second metal layers is changed. As the electric conductivity changes, the oscillator is activated to indicate the necessity for replacing the diaper.

Further, since the metal layers are respectively formed on opposing side surfaces of the water impermeable sheet, and this water sensing means is secured to the both ends of the diaper, this water content sensing means is free from generating a premature signal on account of the breakage as the patient moves heavily.

The metal layers do not need additional manufacturing processes such as lamination of an insulating layer on the metal layer, so that this water sensing means can be assembled to the diaper in the same manufacturing process.

The energy consumption for the device according to the present invention is less than that of the conventional capacitor type water content sensing device. Further, the present invention can provide the diaper with a low cost in comparison with the conventional capacitor type device owing to a simple configuration.

The oscillator for the informing means can be removed from the used diaper, so that only the diaper is disposed and the oscillator will be saved for reuse.

Other objects, features and advantages of the present invention will become apparent upon perusal of the following detailed description of the preferred embodiments of the present invention when taken in conjunction with the appended drawings.

DETAILED DESCRIPTION OF THE PREFERRED EMBODIMENT

Hereinbelow, a preferred embodiment of a water content sensing and informing system for a disposable diaper according to the present invention will be explained in detail with reference to the accompanying drawings.

Figure 1:
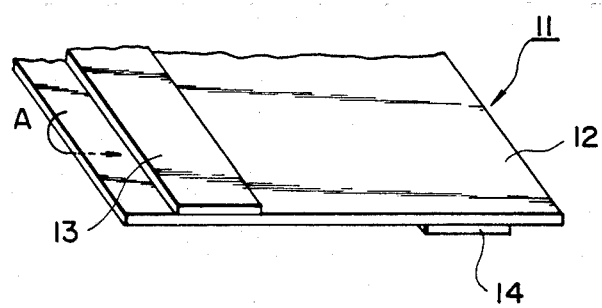
FIG. 1 is a perspective illustration showing an essential portion of the water sensing means which is adapted for a disposable diaper according to the present invention.

Referring to FIG. 1, there is shown a water content sensing section 11, composed of a water impermeable sheet 12, a first metal layer 13 formed on the top surface of the sheet 12 and a second metal layer 14 formed on the bottom surface of the sheet 12.

Preferably, the water impermeable sheet 12 is formed from a water proof treated paper having a thickness of 10 $\mu$m to 150 $\mu$m, or a plastic film having a thickness of 3 $\mu$m to 30 $\mu$m and made of polypropylene, polyethylene, polyester, polyvinyl chloride, or the like.

The metal layers 13 and 14 are formed in a thin layer having a thickness of 15 $\mu$m or less on the sheet 12 by means of lamination or vacuum evaporation of metal material such as aluminium, zinc, copper, tin or nickle. It is preferable to perform vacuum evaporation under a high vacuum condition of $1 \times 10^2$ Torr or more.

Figure 2:
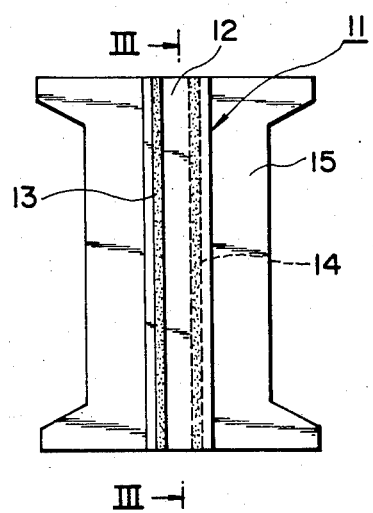
FIG. 2 is a plan view of a disposable diaper with the water content sensing means shown in FIG. 1.
Figure 3:
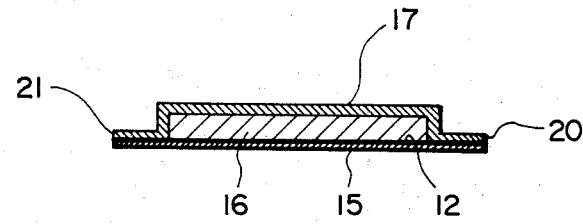
FIG. 3 is a sectional view taken along with the line III—III in FIG. 2.

As shown in FIG. 2, the water content sensing section 11 can be disposed in any suitable position such as at substantially the center of the disposable diaper. The diaper consists of a water impermeable outer sheet 15, a water absorber 16 and a water permeable inner sheet 17. The water absorber 16 is interposed between the outer sheet 15 and the inner sheet 17 as shown in FIG. 3. The water content sensing section 11 is interposed between the outer sheet 15 and the water absorber 16. The longitudinal length of the water content sensing section 11 is substantially equivalent to that of the outer and inner sheets 15, 17 so as to facilitate attachment at both ends 20, 21 by means of a pressure welding or an adhesive as shown in FIG. 3. This step can be performed during the normal assembly process of the disposable diaper. One end of the water content sensing section 11 may be exposed out of the diaper as required.

The water content sensing section 11 is not only interposed between the water absorber 16 and the water impermeable outer sheet 15, but it may be also interposed between the water absorber 16 and the water permeable inner sheet 17 or disposed in the water absorber 16. Preferably, it is interposed between the water absorber 16 and the outer sheet 15. Further, a water permeable or absorbing sheet such as tissue paper (not shown in the drawings) may be disposed between the water content sensing section 11 and the outer sheet 15 in order to facilitate the flow of water to the second metal layer 14 formed on the bottom surface of the sheet 12. Alternatively, the bottom surface of the sheet 12 may be coated with a water absorbing material before forming the metal layer 14.

The water permeable inner sheet 17 is a non-woven sheet with a texture rate of 10 to 30 g/m² made of rayon, polypropylene or polyester fiber. The water absorber 16 is a structural material made of cotton pulp, tissue paper, or super absorbing polymer. The water impermeable outer sheet 15 is a plastic film having its thickness of 15 to 40 μm made of polyethylene, or the like.

Figure 4:
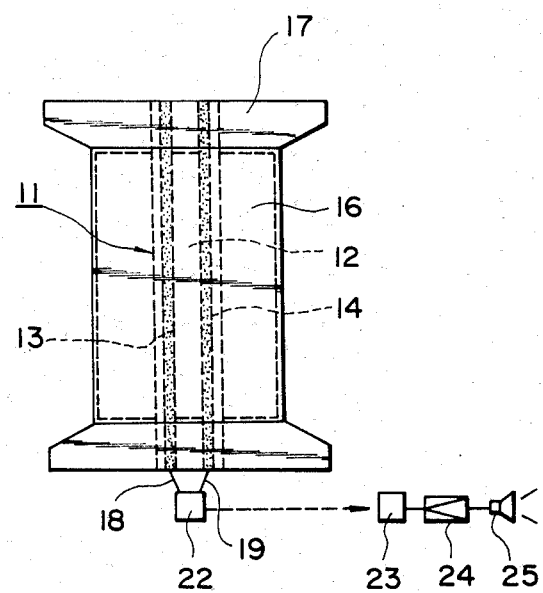
FIG. 4 is a schematic illustration of an embodiment of the informing system according to the present invention.

The first and second metal layers 13 and 14 are electrically connected to a suitable informing device 22 for detecting and informing the appropriate personnel of a change in the electric conductivity between these metal layers through lead wires 18 and 19 as shown in FIG. 4. This informing device will be referred in detail in the following description.

According to the above mentioned configuration, the water content sensing operation will be described as follows.

When the water content of excrement is at a relatively low level, the water is completely absorbed in the water absorber 16. Even when a part of the water reaches to the first metal layer 13 formed on the top surface of the water content sensing section 11, the water quantity is not sufficient to flow toward the bottom surface of the sensing section 11. Thus the electric conductivity between the first and second metal layers 13 and 14 is not varied. Under these conditions, the informing device 22 for detecting the change of electric conductivity does not detect any change of the electric conductivity between the metal layers 13, 14. Therefore the informing device 22 does not transmit a signal representing the necessity for replacing the diaper with a new one.

As the water content in the diaper increases and exceeds a specific level such that the water is not completely absorbed in the water absorber 16, the excess water flows over the edges of the sheet 12 of the water content sensing section 11 as represented by the arrow A shown in FIG. 1 and reaches the second metal layer 14 formed on the bottom surface. The electric conductivity between the two metal layers 13 and 14 is changed owing to the existence of this water. The informing device 22 can detect the change of the electric conductivity and thus outputs an information signal representing the necessity to replace the diaper with a new one.

Referring to FIG. 4, there is shown the embodied diaper provided with the water content sensing means and an example of an informing system for practical application composed of an oscillator. This oscillator, corresponds to the informing device 22 and as before mentioned, is electrically connected to the first and second metal layers 13 and 14 through the lead wires 18 and 19. The oscillator 22 is composed of an electronic circuit which is actuated in response to the change of the electric conductivity between the first and second metal layers 13 and 14. The electronic circuit contains an oscillating function depending on this actuation. A receiver 23 is provided with a circuit for receiving the oscillating signal from the oscillator 22 and is located at a remote place such as a nurse center. The input signal is amplified through an amplifier 24 and finally generated to the appropriate personnel by acoustic means or a visual means through an alarming device 25.

Figure 5:
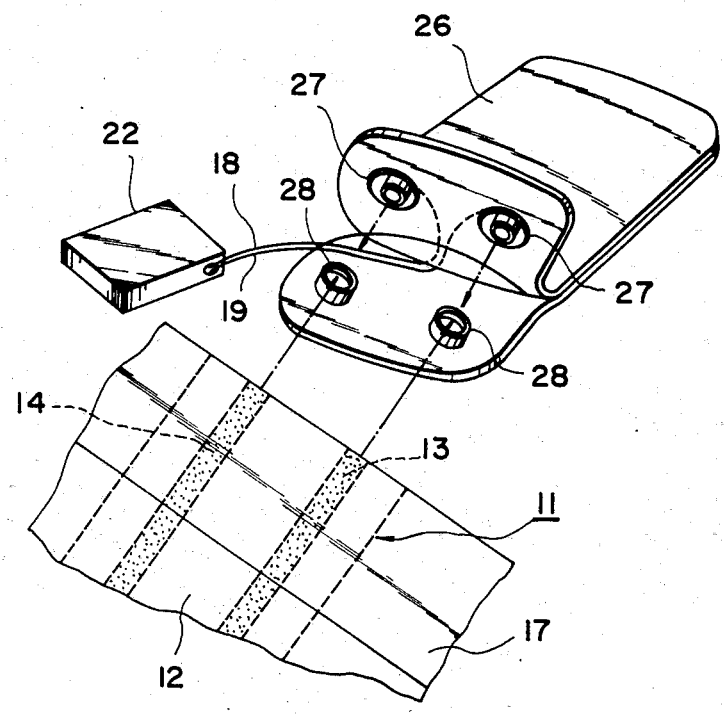
FIG. 5 is a schematic illustration of the oscillator and its water proof case with the mounting device of the diaper.

FIG. 5 shows one manner in which oscillator 22 is attached to the metal layers 13 and 14. The oscillator 22 has lead wires 18 and 19 connected to clip terminals of a water proof case 26. Each clip terminal is composed of a projecting portion 27 and recessed portion 28 which are adapted to engage to each other. One end of the water content sensing section 11, partially exposed out of the diaper, is pressed between the clip terminals, so that the first and second metal layers 13 and 14 are electrically connected to the oscillator 22.

For practical use, the oscillator 22 is totally packed in the water proof case 26, and the case 26 is attached to the diaper through the clip terminals. This water proof case 26 is made of a water resistant material such as synthetic resin or artificial leather. The clip terminals are treated with nickel or chrome plating to resist corrosion. In order to securely fasten the water proof case 26 and the metal layers 13 and 14, additional projections may be formed on the clip terminals.

Figure 6:
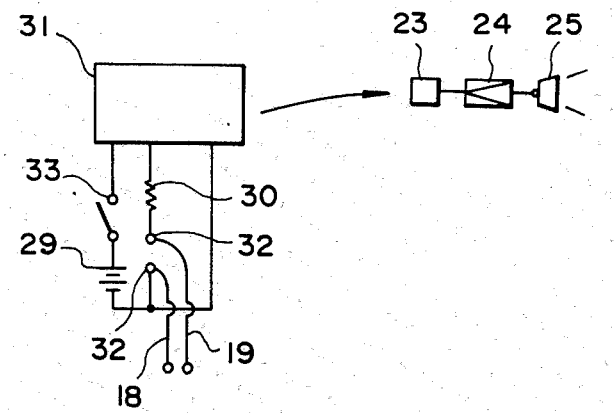
FIG. 6 is a circuit diagram of the informing system shown in FIG. 4.
Figure 7:
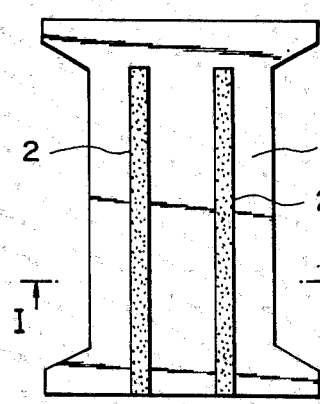
FIG. 7 is a plan view showing an example of a conventional water sensing diaper wherein a pair of metal layers are formed on the water impermeable outer sheet of the diaper.
Figure 9:
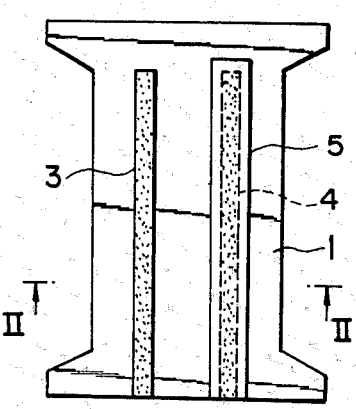
FIG. 9 is a plan view showing another example of conventional water sensing diaper which is of a capacitor type sensing means formed on the water impermeable outer sheet.
Figure 8:
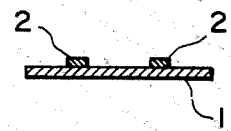
FIG. 8 is a sectional view taken along with the line I—I shown in FIG. 7.
Figure 10:
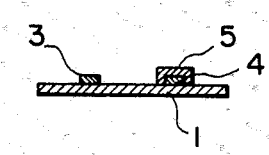
FIG. 10 is a sectional view taken along with the line II—II shown in FIG. 9.

FIG. 6 shows an example of a structure of the oscillator 22, which contains a DC power source 29 such as a button cell, a resistor 30, an oscillating circuit 31, terminals 32, the lead wires 18 and 19 connected to terminals 32, and a switch 33.

As the water flows and reaches to the second metal layer 14, during which the switch 33 is kept in its ON-position, the power is applied to the oscillating circuit 31 in response to the change of the electric conductivity between the metal layers 13 and 14. The oscillating circuit 31 generates an oscillating output signal. This output signal is received by the receiver 23 located at the remote place. According to this water content sensing and informing system, the nursing person can easily determine the necessity for replacing the diaper with a new one.

It should be appreciated while the various embodiments of the present invention have been described in specific detail, numerous additions, ommissions and modifications are possible within the intended spirit and scope of the invention.

What is claimed is:

1. A liquid content sensing and informing system for use with a disposable diaper including a liquid permeable inner liner, a liquid absorber, and a liquid impermeable outer liner, the system comprising:

(a) a liquid content sensing means consisting of a liquid impermeable sheet having a width less than said liners, upper and lower surfaces, first and second ends, and first and second side edges,
(b) first and second metal layers,
(c) means for securing said first metal layer to said upper surface of said liquid impermeable sheet,
(d) means for securing said second metal layer to said lower surface of said liquid impermeable sheet,
(e) said liquid impermeable sheet of said liquid content sensing means being positioned intermediate the liquid permeable inner liner and the liquid impermeable outer liner of the disposable diaper,
(f) means for securing said first and second ends of said liquid impermeable sheet to the disposable diaper permitting excess liquid accumulated in said diaper when saturated to flow over the first and second side edges of said liquid impermeable sheet for interacting said first metal layer with said second metal layer, and
(g) informing means electrically connected to said first and second metal layers, in response to change of the electric conductivity between said first and second metal layers resulting from to flow of liquid therebetween, for indicating that the liquid content of substantially the entire diaper has exceeded the saturated state.

2. A liquid content sensing and informing system as in claim 1, wherein:
(a) said liquid content sensing means is disposed in said liquid absorber.

3. A liquid content sensing and informing system as in claim 1, wherein:
(a) said liquid content sensing means is disposed between said liquid permeable inner liner and said liquid absorber.

4. A liquid content sensing and informing system as in claim 1, wherein:
(a) said liquid sensing means is disposed between said liquid absorber and said liquid impermeable outer linner.

5. A liquid content sensing and informing system as in claim 1, wherein:
(a) said liquid content sensing means has a longitudinal length substantially equal to the longitudinal length of the diaper for permitting simultaneous attachment of the liquid content sensing means, the liquid permeable inner linner, the liquid absorber and the liquid impermeable outer liner during the assembly process.

6. A liquid content sensing and informing system as in claim 5, wherein:
(a) said means for securing said liquid content sensing means includes at least one of pressure welding and an adhesive.

7. A liquid content sensing and informing system as in claim 1, wherein:
(a) said metal layers are formed in a thin layer on said liquid impermeable sheet by means of lamination or vacuum evaporation of metal leaf having a thickness of less than 15 $\mu$m, and
(b) said metal layers being formed from one of aluminum, zinc, copper, tin, and nickel.

8. A liquid content sensing and informing system as in claim 1, wherein:
(a) said informing means includes an oscillator which is activated in response to the change of the electric conductivity between said first and second metal layers, a receiver for receiving the output signal from the oscillator, and an accoustic or visual informing device, activated by the output from the receiver, for indicating the necessity for replacing the diaper.

9. A liquid content sensing and informing system as in claim 8, wherein:
(a) said receiver is located in a place remote from the oscillator.

10. A liquid content sensing and informing system as in claim 9, wherein:
(a) said informing means includes at least one lead wire for electrically connecting said oscillator to said first and second metal layers.

11. A liquid content sensing and informing system as in claim 1, wherein:
(a) said informing means includes a liquid impermeable container for encasing said oscillator, and
(b) said container includes means for detachably connecting it to the diaper.

12. A liquid content sensing and informing system as in claim 11, wherein:
(a) said detachment means includes at least one clip terminal electrically connected to one of said first and second metal layers, and
(b) said at least one clip terminal includes a corrosion resistance layer.

13. A liquid content sensing and informing system as in claim 12, wherein:
(a) said corrosion resistance layer is formed from one of nickle plating and chrome plating.

* * * * *